(12) United States Patent
Boquet

(10) Patent No.: US 8,834,010 B2
(45) Date of Patent: Sep. 16, 2014

(54) DEVICE FOR THE QUICK VIBRATION OF TUBES CONTAINING, IN PARTICULAR, BIOLOGICAL SAMPLES

(75) Inventor: Jean Boquet, Le Perray En Yvelines (FR)

(73) Assignee: Bertin Technologies (FR)

( * ) Notice: Subject to any disclaimer, the term of this patent is extended or adjusted under 35 U.S.C. 154(b) by 75 days.

(21) Appl. No.: 13/508,675

(22) PCT Filed: Nov. 10, 2010

(86) PCT No.: PCT/FR2010/052414
§ 371 (c)(1),
(2), (4) Date: Jun. 26, 2012

(87) PCT Pub. No.: WO2011/058278
PCT Pub. Date: May 19, 2011

(65) Prior Publication Data
US 2012/0263010 A1    Oct. 18, 2012

(30) Foreign Application Priority Data

Nov. 10, 2009   (FR) ..................................... 09 05389

(51) Int. Cl.
| | | |
|---|---|---|
| *B01F 11/00* | (2006.01) | |
| *B01F 7/00* | (2006.01) | |
| *C12M 3/06* | (2006.01) | |
| *B01F 13/10* | (2006.01) | |
| *B01L 9/06* | (2006.01) | |

(52) U.S. Cl.
CPC ..... *B01F 11/0008* (2013.01); *B01F 2215/0073* (2013.01); *B01F 11/0097* (2013.01); *B01F 11/0028* (2013.01); *B01F 2215/0037* (2013.01); *B01F 2013/1083* (2013.01); *B01L 9/06* (2013.01); *C12M 27/16* (2013.01)

USPC ........... 366/111; 366/110; 366/197; 366/216; 366/218

(58) Field of Classification Search
USPC ......... 366/213, 214, 215, 216, 110, 111, 197, 366/218
See application file for complete search history.

(56) References Cited

U.S. PATENT DOCUMENTS 5,238,304 A * 8/1993 Zimmermann ............... 366/216
5,567,050 A   10/1996 Zlobinsky et al.
(Continued)

FOREIGN PATENT DOCUMENTS

FR   2 839 267 A1   11/2003
GB     684615 A    12/1952
(Continued)

OTHER PUBLICATIONS

International Search Report and Written Opinion for International Application No. PCT/FR2010/052414, mailed Feb. 18, 2011.

*Primary Examiner* — Tony G Soohoo
*Assistant Examiner* — Anshu Bhatia
(74) *Attorney, Agent, or Firm* — Alston & Bird LLP

(57) ABSTRACT

An appliance for rapidly vibrating test tubes containing samples to be ground up, the appliance comprising an electric motor (12) for driving rotation of a disk (16) that is provided with an eccentric pin (17), the appliance being characterized in that the test tubes (23) are perpendicular to the eccentric pin and are held by a clamp (21) mounted on a support (20) that is substantially parallel to the eccentric pin, being connected to a fixed baseplate via a Cardan type hinge (15) having two mutually perpendicular axes of rotation (X and Y), one of which axes (Y) is substantially parallel to the eccentric pin (17) and connects the support (20) to the other axis (X) of the hinge (15) that prevents the support (20) from moving in rotation about a perpendicular axis (Z). The support (20) is connected to the eccentric pin (17) by a link (19).

14 Claims, 3 Drawing Sheets

(56) References Cited

U.S. PATENT DOCUMENTS

| | | | |
|---|---|---|---|
| 5,707,861 A | 1/1998 | Sherman et al. | |
| 6,235,245 B1 * | 5/2001 | Sherman et al. | 366/213 |
| 6,235,501 B1 | 5/2001 | Gautsch et al. | |
| 7,810,989 B2 * | 10/2010 | Little | 366/215 |

FOREIGN PATENT DOCUMENTS

| | | |
|---|---|---|
| WO | WO 2004/012851 A2 | 2/2004 |
| WO | WO 2004/105925 A1 | 12/2004 |
| WO | WO 2008/000962 A2 | 1/2008 |

* cited by examiner

DEVICE FOR THE QUICK VIBRATION OF TUBES CONTAINING, IN PARTICULAR, BIOLOGICAL SAMPLES

FIELD OF THE INVENTION

The invention relates to an appliance for rapidly vibrating test tubes containing samples, in particular biological samples, the rapid vibration of the test tubes serving to grind up, stir, and/or homogenize the samples.

BACKGROUND

It is already known to grind up biological samples (tissues, cereals, hair, etc.) by enclosing the samples in test tubes that also contain micro-beads of glass, ceramics, steel, or other material, and by subjecting the hermetically sealed test tubes to essentially axial vibration at high frequency, e.g. at about 100 hertz (Hz), for a relatively short duration, of the order of 30 seconds (s) to 60 s, for example.

Various documents such as U.S. Pat. No. 5,567,050 and WO 2004/012851 describe appliances for performing such a method. They comprise a circular tray supporting the tubes and means for driving the tray with oscillatory motion about a center of rotation.

The tubes are fastened to the periphery of the tray at the same distance from the center of rotation, and they are thus moved in substantially curvilinear reciprocating motion.

Theoretically, the speed of rotation of the outlet shaft from the motor lies in the range 3000 revolutions per minute (rpm) to 8000 rpm, and the samples are subjected to linear accelerations lying in the range 150 g to 400 g in order to grind them up.

However those appliances work on a large number of samples simultaneously (in general 12, 16, 24, or 48 samples).

Those appliances are intended for large laboratories that need to analyze a large quantity of samples on a continuous basis, and generally while using the same protocol. A typical example is the laboratories that are incorporated in slaughterhouses for cattle and that serve to detect BSE. Those laboratories need to analyze a sample of the brain of each beast and to give the results of the analysis before the carcass leaves the slaughterhouse. That may represent more than 1000 analyses per day.

Many laboratories are not that specialized. They might need to grind up or stir a sample only one or two times a day or even less often, and they need to work in succession on different samples that require different protocols.

Those laboratories may also need to work on samples of different volumes, and consequently contained in test tubes of different sizes, e.g. 2 microliters (µL) and 7 µL.

For those laboratories, which are very numerous, using a 16 or 24 test-tube machine is possible, but not cost effective.

SUMMARY

A particular object of the present invention is to provide a solution to that problem that is simple, effective, and inexpensive.

The invention provides an appliance of the above-specified type that enables rapid vibration to be imparted to a few tubes containing samples for analysis with quality and effectiveness that are at least equivalent to the quality and effectiveness of known appliances.

The invention also provides an appliance that can function without damage at high frequencies.

The invention also provides an appliance of small size, that is simple to use and to maintain, and that can easily be placed on a laboratory bench top.

To this end, the invention provides an appliance for rapidly vibrating test tubes containing samples to be ground up, the appliance comprising an electric motor for driving rotation of a disk that is provided with an eccentric pin, the appliance being characterized in that the test tubes are carried by a support substantially parallel to the eccentric pin and are oriented substantially perpendicularly to the eccentric pin, which pin is connected to a fixed baseplate via a hinge center having two mutually perpendicular axes of rotation, one of which axes is substantially parallel to the eccentric pin and connects the support to the other axis of the hinge center that prevents the support from moving in rotation about an axis perpendicular to the two above-mentioned axes.

The appliance of the invention thus comprises a test-tube support and means for driving the support to perform oscillatory motion about a hinge center, the test-tube support being connected to a stationary portion of the appliance via a connection having two orthogonal degrees of freedom in rotation about axes X and Y in a rectangular frame of reference, thereby enabling said support to perform oscillatory motion about the hinge center while remaining at a constant distance from the hinge center.

The vibratory movement of the test-tube support as generated by a rotating disk having an eccentric pin is transmitted to said support by a link fastened thereto via a fork having a hinge axis that is transverse or orthogonal to the length direction of the support. The motion transmitted to the test tubes containing the samples thus has a figure-of-eight shaped path over a surface that is substantially spherical. This path has the feature of causing the beads to sweep fully over the inside of the test tubes and of grinding up the samples effectively.

Preferably, the hinge center of the test-tube support is embodied by a Cardan type hinge, a fork, a strip of elastomer or of polymer, or a row of elastomer studs.

The link is connected to the pin of the rotary disk by a rolling ball joint. Its fork fastened to the support enables it to adapt to deformations that result from the relative movements between the pin of the driving disk and the support. Its effective length is substantially identical to the distance between its fastening point on the support and the hinge center of the support on the appliance.

In an embodiment, the assembly comprising the hinge center, the support, and the link is made as a single piece of metal, of elastomer, or of polymer. Inserts, put into place while molding or casting the part, serve to provide better stiffness in rotation about an axis Z, while allowing the movements to take place about the axes X and Y and while also providing a small amount of capacity for the link to adapt to the path followed by the pin of the rotary disk.

According to other characteristics of the invention, the test tubes are held on the support by means of clamps. Advantageously, they may be slightly inclined in order to encourage the beads to sweep the inside volumes of the test tubes fully.

In a basic configuration, the support is fitted with a set of clamps capable of receiving one, two, or three test tubes of small volume, e.g. 2 mL, and/or one test tube of large volume, e.g. 7 mL.

In a preferred embodiment, the rotary disk is driven in rotation by an electric motor for which the user can set both the speed of rotation, e.g. in the range 3000 rpm to 7000 rpm, and also the duration of operation, e.g. in the range 30 s to 180 s.

In two variants that function in the same way, the link, the rotary disk, and the motor are placed below or above the test-tube support.

BRIEF DESCRIPTION OF THE INVENTION

The invention can be better understood and other characteristics, details, and advantages thereof appear more clearly on reading the following description made by way of example with reference to the accompanying drawings, in which.

Figure 3A:
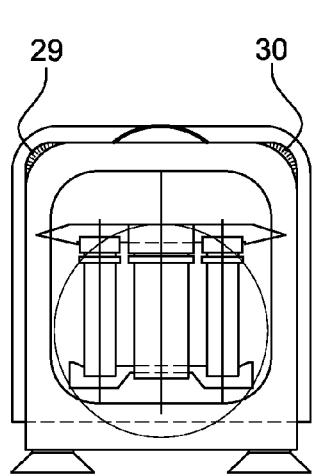
Figure 3B:
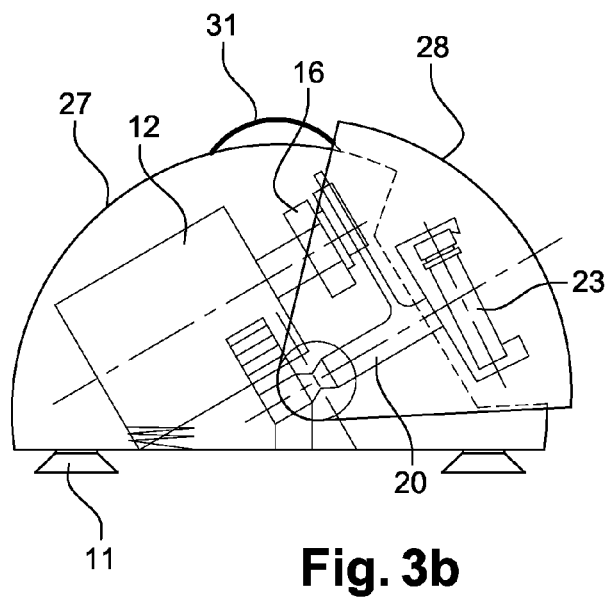
Figure 4:
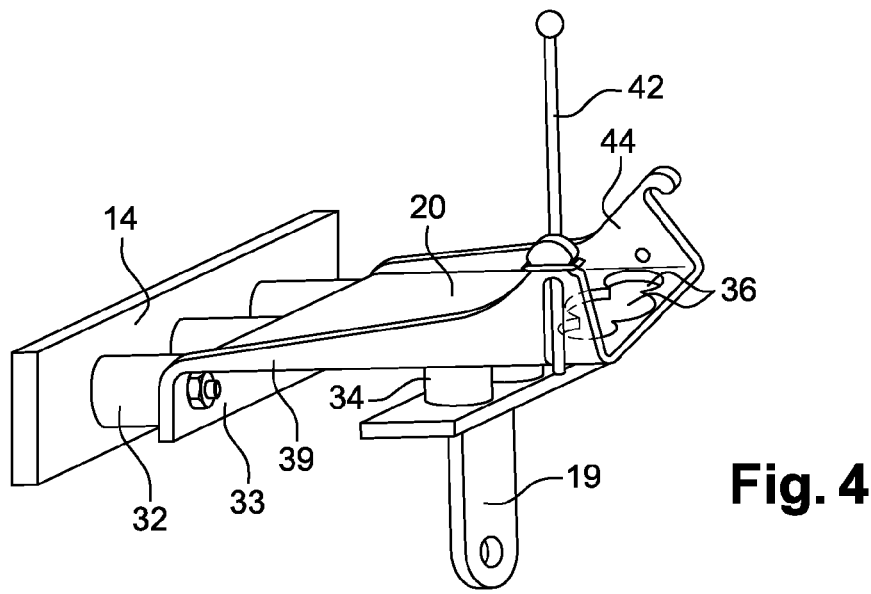
Figure 5:
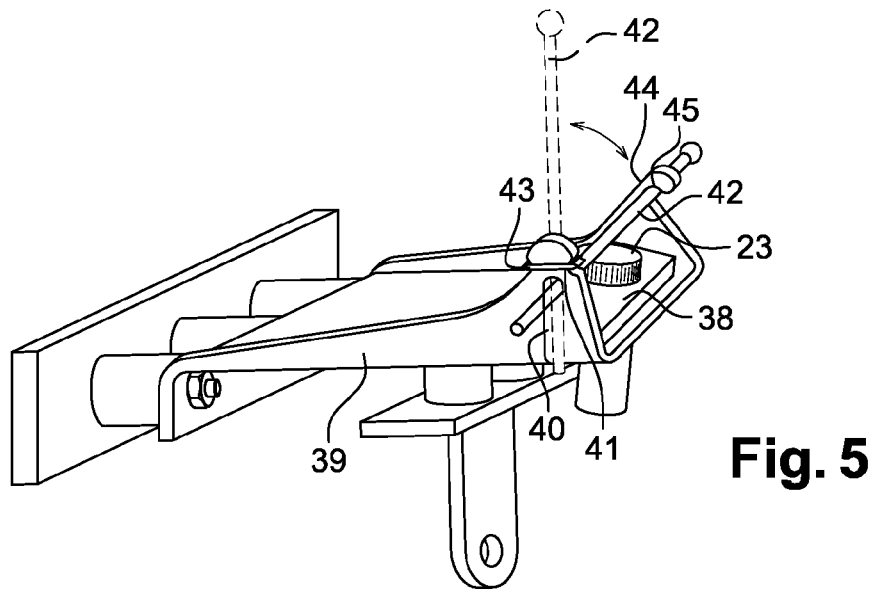
Figure 6A:
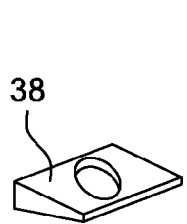
Figure 6B:
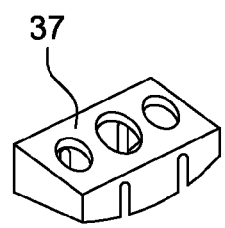

FIGS. 3*a* and 3*b* are a face view and a side view of an example of how the components can be arranged and how the appliance can be made;

FIGS. 4 and 5 are diagrammatic perspective views of variant embodiments; and FIGS. 6*a* and 6*b* are diagrammatic perspective views of variant embodiments of spacers for supporting and positioning test tubes.

DETAILED DESCRIPTION

Figure 1:
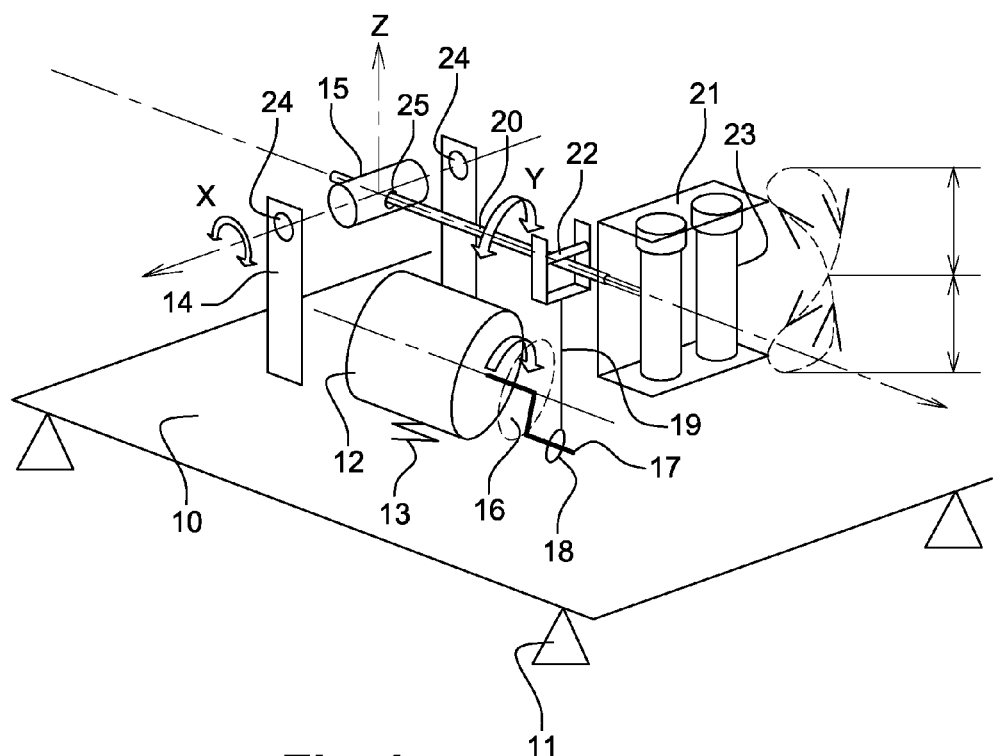
FIG. 1 is a diagrammatic perspective view of an embodiment of an appliance of the invention without its covering.

In the embodiment of FIG. 1, the appliance of the invention comprises a baseplate 10 having its bottom portion provided with insulating legs 11 for standing on a laboratory bench top or some other plane stationary support, and having its top portion receive an electric motor 12 via a vibration-filtering connection 13 and a support 14 for a hinge center 15.

A disk 16 that is fastened on the shaft of the motor 12 is provided with an eccentric pin 17 on which a link 19 is fastened via a rolling ball joint 18.

The link 19 is fastened to a support 20 via a fork 22 capable of imposing rotary motions on the support 20 about two mutually perpendicular axes X and Y that define the hinge center 15 where they intersect.

The hinge 15 is fastened to the support 14 by bearings 24, preferably ball bearings, that prevent axial movement and that allow a single degree of freedom in rotation about the axis X.

The support 20 is fastened to the hinge 15 by a bearing 25, preferably a ball or roller bearing that prevents axial movement and that allows a single degree of freedom in rotation about the axis Y.

A clamp 21 for receiving and holding test tubes 23 is fastened rigidly to the support 20. It is capable of receiving a small number of test tubes, e.g. a number lying in the range 1 to 5.

Figure 2:
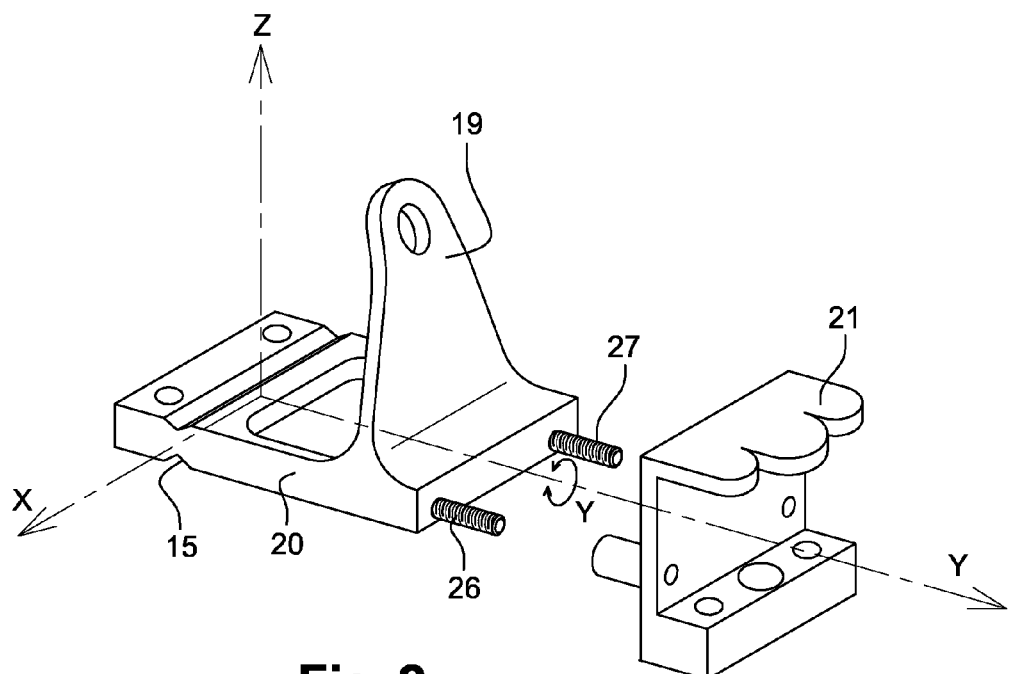
FIG. 2 is a diagrammatic perspective view of the assembly comprising the hinge center, the support, the link, and the test-tube clamps.

In the embodiment shown in FIG. 2, the support 20, the hinge center 15, and the link 19 are made as a single piece of polymer or elastomer. Stiffeners 26 are inserted in the support to facilitate hinge movements about the axes X and Y of the hinge center 15 and to prevent movements in rotation about the axis Z perpendicular to the axes X and Y. The material constituting the support is selected to provide great ability to withstand successive flexing of the hinge 15.

The major advantages of this embodiment are the low cost of fabrication and maintenance and the significant reduction in the level of noise due to the absence of mechanical parts.

The embodiment shown in FIGS. 3*a* and 3*b* uses the support 20 of FIG. 2. The motor 12 is placed obliquely above the support 20 and the test tubes 23 that are inclined relative to the vertical. This arrangement makes it possible to provide an appliance that is compact and ergonomic. The assembly is placed under a cover 27 that includes a visor 28. Tilting the visor 28 rearwards gives access to the test tubes 23 and to the knobs 29 and 30 for adjusting the speed of rotation of the motor and the duration of operation. It also prevents access to the button 31 for switching the motor on and off.

Tilting the visor forwards, protects the operator and the environment, preventing access to the test tubes 23 and to the knobs at 29 and 30, thereby preventing any change to the settings of the operating parameters, while also giving access to the button 31 for switching the appliance on and for switching it off early, if necessary.

In the embodiment shown in FIG. 4, the support 20 and the clamp 21 for receiving the test tubes 23 are made as a single plate of lightweight metal or of rigid plastics material constituted by a flat, an edge at right angles 33, and two stiffener flanks 39 and 44. The hinge center 15 is constituted by a row of three elastomer studs 32 fastened by screw fastening or by vulcanization at one of their ends to a fixed support 14 and at their other ends to the right-angled edge 33 of the support 20. The studs are mutually parallel and parallel to the axis Y. In a variant, the outer two studs may be parallel to the axis Y and the central stud may be parallel to the axis Z, their centers of rotation being in alignment on the axis X so as to encourage the support 20 to move in rotation about the axes X and Y, while limiting movements relative to the axis Z.

The link 19 is fastened to the support 20 via a row of three elastomer studs 34 that are fastened by screw fastening or by vulcanization at one of their ends to the support 20 and at their other ends to a right-angled portion of the link 19.

The 2 mL or 7 mL test tubes 23 are engaged and held in holes 36 formed in the front of the support 20.

In the embodiment shown in FIGS. 5, 6*a*, and 6*b*, the 2 mL or 7 mL test tubes 23 are positioned and held in the holes 36 by means of spacers 37 or 38 that are advantageously biased so as to cause the test tubes to slope a little relative to the plane of the support 20. The spacer 37 is adapted to receive one, two, or three 2 mL tubes. The spacer 38 is adapted to receive one 7 mL tube.

One of the flanks 39 of the support 20 includes a slot 40 and notches 41. A rod 42 made of glass or of carbon fiber, for example, is provided with an elastomer ring 43. The ring 43 is positioned in the notches 41, and the rod 42 is positioned in the slot 40, in such a manner that the rod 42 is held in a vertical position by the ring 43.

The other flank 44 includes a hook 45 for receiving the other end of the rod 42.

The or each test tube may be prevented from moving on the support 20 by means of the wedges 37 or 38 and of the rod 42 that curves between the slot 40 and the hook 45.

In the embodiment of FIG. 6*b*, in order to guarantee uniform clamping when using two or three 2 mL test tubes, the spacer 37 is split between the orifices for receiving the test tubes so as to enable it to deform and adapt automatically to any variations in the heights of the test tubes. Advantageously, the deformation of the ends of the spacer causes the end test tubes to converge, which is favorable to obtaining grinding of uniform quality in the various test tubes. A spacer 37 may also be designed to receive two 2 mL test tubes at its ends and one 7 mL test tube in the middle

The invention claimed is:

1. An appliance for rapidly vibrating test tubes containing samples to be ground up, which comprises an electric motor for driving rotation of a disk that is provided with an eccentric pin, wherein the test tubes are carried by a support substantially parallel to the eccentric pin and are oriented substantially perpendicularly to the eccentric pin, which eccentric pin is connected to a fixed baseplate via a hinge center having a first and a second mutually perpendicular axes of rotation, the first axis of rotation being substantially parallel to the eccentric pin and connecting the support at a first end to the second axis of rotation of the hinge center that prevents the support from moving in rotation about a third axis of rotation perpendicular to the first and second axes of rotation, and wherein the support is connected to the eccentric pin by a link having:
- a first end connected to the support by a fork-type connection which defines a Cardan type coupling with the support and is adapted for imposing a vibratory movement on said support about both said first and second axes of rotation, and
- a second end connected to the eccentric pin.

2. The appliance according to claim 1, wherein at said second end, the fork-type connection includes a hinged connection to the eccentric pin.

3. The appliance according to claim 2, wherein the hinged connection comprises a rolling ball joint.

4. The appliance according to claim 1, wherein rotation of the disk drives vibratory movement of the tubes about the second axis of rotation associated with rotary movement about the first-axis of rotation, the first and second axes of rotation being perpendicular relative to each other where they intersect.

5. The appliance according to claim 2, wherein the link and the fork-type connection are in the form of a part made of metal or of an elastically-deformable material.

6. The appliance according to claim 2, wherein the support is made as a single part together with the link and the fork-type connection.

7. The appliance according to claim 2, wherein the support is made as a single part together with the link, the fork-type hinge, and the hinge center.

8. The appliance according to claim 1, wherein the hinge center is formed by a Cardan type joint, by a fork, by a strip of elastomer or of polymer, or by a row of elastomer studs.

9. The appliance according to claim 1, wherein the motor and the eccentric pin extend obliquely above the support and the test tubes that are inclined relative to the vertical.

10. The appliance according claim 1, wherein the speed of rotation of the disk carrying the eccentric pin lies in the range 3000 rpm to 7000 rpm.

11. The appliance according to claim 1, wherein the support carries one to five test tubes.

12. The appliance according to claim 1, wherein said first and second axes of rotation define the hinge center where they intersect.

13. The appliance according to claim 2, wherein the link is perpendicular to the support.

14. The appliance according to claim 1, wherein each of the link and the support comprises an elongate rod.

* * * * *